United States Patent [19]

Lee et al.

[11] Patent Number: 5,583,268

[45] Date of Patent: Dec. 10, 1996

[54] METHOD TO PREPARE ORTHO SUBSTITUTED PHENOL

[75] Inventors: Guo-shuh J. Lee; Juan M. Garces; Dennis A. Hucul, all of Midland; Tracy L. Young, Chesaning; Kenneth A. Burdett, Midland, all of Mich.

[73] Assignee: The Dow Chemical Company, Midland, Mich.

[21] Appl. No.: 573,091

[22] Filed: Dec. 15, 1995

[51] Int. Cl.⁶ .................................................. C07C 39/12
[52] U.S. Cl. .......................... 568/744; 568/731; 568/772; 568/790; 568/794
[58] Field of Search ................................. 568/744, 790, 568/791, 731, 772

[56] References Cited

U.S. PATENT DOCUMENTS

| | | |
|---|---|---|
| 3,290,389 | 12/1966 | Hahn . |
| 3,367,981 | 2/1968 | Napolitano . |
| 3,426,358 | 2/1969 | Schlichting et al. . |
| 3,670,030 | 6/1972 | Sparks . |
| 4,060,559 | 11/1977 | Goto et al. . |
| 4,080,390 | 3/1978 | Imamura . |
| 4,088,702 | 5/1978 | Goto et al. . |
| 4,260,833 | 4/1981 | Firth . |
| 4,398,048 | 8/1983 | Firth . |
| 4,451,676 | 5/1984 | Everly .................................. 568/790 X |
| 4,599,465 | 7/1986 | Tamaru et al. . |
| 4,731,492 | 3/1988 | Wiker et al. . |
| 4,798,911 | 1/1989 | Lentz et al. ......................... 568/772 X |
| 5,041,692 | 8/1991 | Ungarelli et al. ....................... 568/744 |
| 5,043,483 | 8/1991 | Sogli et al. ............................ 568/744 |
| 5,072,054 | 12/1991 | Marler et al. .......................... 568/794 |
| 5,292,970 | 3/1994 | Kupper et al. ......................... 568/794 |
| 5,344,997 | 9/1994 | Kocal ................................. 568/731 X |

FOREIGN PATENT DOCUMENTS

| | | |
|---|---|---|
| 083423 | 4/1974 | Japan . |
| 117314 | 7/1974 | Japan . |
| 925819 | 5/1963 | United Kingdom . |

*Primary Examiner*—Paul F. Shaver

[57] ABSTRACT

A process of catalytically reacting a 3–18 carbon monoolefin such as cyclohexene with an arylhydroxide such as phenol in the liquid phase forming an ortho-alkylated arylhydroxide which is subsequently catalytically dehydrogentated to form an ortho-alkenylarylhydroxide or ortho-arylarylhydroxide such as ortho-phenylphenol.

22 Claims, No Drawings

METHOD TO PREPARE ORTHO SUBSTITUTED PHENOL

FIELD OF THE INVENTION

This invention relates to the formation of an ortho substituted arylhydroxide by an improved process. In particular, the invention relates to an improved process to form ortho-phenylphenol.

BACKGROUND OF THE INVENTION

Ortho-phenylphenol (OPP) has been used as a germicide, disinfectant, citrus fruit preservative and dye intermediate.

OPP has been synthesized by several methods. The methods have either used expensive reactants or resulted in low OPP yields as a result of low conversion or low selectivity. The percent conversion of a reactant is 100 times the ratio of moles of the reactant converted into product or by-product over the initial moles of the reactant. Percent selectivity is 100 times the ratio of the moles of a reactant converted into a desired product over the moles of said reactant converted into product or by-product.

OPP has been formed by reacting sodium phenylate with diphenyl oxide in an ethereal solvent (Luttringhaus in *Annelen* 542 (1939) 241). The reaction yields about 48 percent OPP.

Basic hydrolysis of ortho-chlorobiphenyl using a cupric oxide catalyst results in an 83 percent OPP yield. However, because the typical route to ortho-chlorobiphenyl, chlorination of biphenyl (e.g., U.S. Pat. No. 1,925,367) has poor ortho selectivity, the overall yield of OPP from the biphenyl is significantly less than 83 percent.

Catalytic hydrogenation of dibenzofuran yields 80 percent phenylphenol conversion with 90 percent of the phenylphenol being OPP (Japanese Patent No. 58-180,448). The catalyst, 0.5–1 percent platinum on alumina, has been reported to suffer from a short lifetime.

Self condensation of cyclohexanone to a mixture of cyclohexenyl cyclohexanone and cyclohexylidenyl cyclohexanone followed by catalytic dehydrogenation to OPP is known. The self condensation reaction conversion to the above mixture is 50 percent and the catalytic yield of OPP is greater than 98 percent. The OPP overall conversion is, of course, the product of the two reactions and it is important to note that cyclohexanone is an expensive reactant.

Therefore, it would be desirable to provide a cost effective high yield method to produce ortho-phenylphenol.

SUMMARY OF THE INVENTION

This invention is a process to prepare a mono-ortho-arylarylhydroxide or mono-ortho-alkenylarylhydroxide, the process comprising (i) alkylating an arylhydroxide having an unsubstituted ortho position with a 2 to 18 carbon olefin in the presence of an alkylating catalyst at a temperature from about 100° C. to about 300° C., a mole ratio of the arylhydroxide to olefin ranging from about 0.5:1 to about 5:1 and a pressure sufficient to form an intermediate product of a mono-ortho-alkylated arylhydroxide and (ii) dehydrogenating said mono-ortho-alkylated arylhydroxide in the presence of a dehydrogenating catalyst at a temperature and under conditions sufficient to form a mono-ortho-alkenylarylhydroxide or a mono-ortho-arylarylhydroxide.

DETAILED DESCRIPTION OF THE INVENTION

The first step of the present invention is the catalytic alkylation of an arylhydroxide by an olefin resulting in the formation of an intermediate product of a mono-ortho-alkylated arylhydroxide, hereinafter referred to as the intermediate product or the mono-ortho-alkylated arylhydroxide. The arylhydroxide can be any arylhydroxide having an unsubstituted ortho position in which the ortho position can be alkylated. Representative examples include ortho-cresol, meta-cresol, para-cresol, p-chlorophenol, o-chlorophenol, p-bromophenol, 4-methoxyphenol, o-ethylphenol, p-ethylphenol and the like. The most preferred arylhydroxide is phenol. The olefin can be any olefin which reacts with phenol to make an alkylated phenol. Preferably the olefin is an olefin hydrocarbon containing 2–18 carbon atoms in which the olefin contains a reactive mono-olefin group such as ethylene, propylene, isobutylene, n-butene, n-pentene, 3-methyl-1-pentene, 2-ethyl-1-hexene, 1-octene, 1-dodecene, 2-ethyl-1-decene, styrene, alpha-methyl styrene, cyclopentene, cyclohexene, cyclohexadiene, cyclooctene and a combination thereof. Preferably the olefin is a cyclo-olefin and more preferably cyclohexene.

Commercially available arylhydroxide and olefin reactants can be used. To enhance the conversion of the alkylation step it may be desirable to remove water from the reactants. Preferably the water present in the arylhydroxide and olefin is less than about 250 ppm (parts per million by weight), more preferably less than about 150 ppm, and most preferably less than about 50 ppm. The water may be removed by any convenient method such as distillation and dessication using, for example, molecular sieves.

The mole ratio of the arylhydroxide to the olefin fed to the reactor affects, for example, the amount of conversion and by-products formed. The arylhydroxide to olefin mole ratio is between about 0.5:1 to about 5:1. Preferably the mole ratio is from about 1:1 to about 2:1, more preferably from about 1:1 to about 1.5:1, and most preferably from about 1:1 to about 1.1:1.

The alkylation of an arylhydroxide is conducted in the presence of an alkylating catalyst. Preferably the alkylating catalyst is an alumina which catalyzes the alkylation of phenols by reaction with an olefin, such as those catalysts described in U.S. Pat. Nos. 3,290,389; 3,367,981; 3,670,030 and 4,500,465, each incorporated herein by reference. Preferably the alumina catalyst is a gamma alumina. It is also desirable for the gamma alumina to be activated at about 400° C. to about 850° C. for a time from about 5 minutes to about 100 hours before being used in the reaction of this invention. The gamma alumina is preferably a product of water and an organo aluminum compound such as an aluminum alkoxide; examples include aluminum ethoxide, aluminum iospropoxide, aluminum sec-butoxide and aluminum tert-butoxide. The gamma alumina preferably has a metal impurity level of less than 500 ppm and a surface area of between about 100 m²/g to 300 m²/g. Suitable gamma alumina catalysts are available commercially under tradenames such as CATAPAL G™.

The alkylation of the arylhydroxide with an olefin according to this invention can be conducted in a continuous or batch pressure reactor containing an alkylating catalyst. Preferably the reactor is a continuous reactor such as a tube reactor. The alkylating catalyst can be present in any form in the reactor such as a powder, spheres, cylinders or other geometries. The reaction can be performed with the catalyst as a particulate suspended in the arylhydroxide and olefin reactants, but it is preferred to have the reactants flow through a catalyst packed bed, particularly, in a continuous reactor.

The arylhydroxide and olefin reactants may be mixed together before being introduced to a reactor or introduced to the reactor separately, and then reacted to form the mono-ortho-alkylated arylhydroxide. When the reactants are introduced separately, mixing occurs within the reactor. The reactor is desirably maintained at a pressure sufficient to maintain the reactants in the liquid state wherein the selected pressure is dependent on the reactant and product vapor pressure at a given reaction temperature. Preferably the pressure is maintained from about 100 psi to 1000 psi and the temperature of the reaction is from at least about 100° C., preferably at least about 150° C., and more preferably at least about 180° C. to at most about 300° C., preferably at most about 250° C., and more preferably at most about 230° C. The reactants are contacted with the gamma alumina catalyst for a time sufficient to form the mono-ortho-alkylated arylhydroxide. Preferably the contact time is at least 5 minutes, more preferably at least 15 minutes and most preferably at least 20 minutes to at most about 4 hours, preferably at most about 2 hours, and more preferably at most about 1 hour.

The intermediate product of a mono-ortho-alkylated arylhydroxide may contain, in addition to the said hydroxide, for example, unreacted olefin and arylhydroxide and by-products. Before dehydrogenating the intermediate product, one or more of by-products, unreacted arylhydroxide or unreacted olefin may be removed by any convenient means, if desired, but such removal is not necessary to perform the process of this invention. Convenient means to remove said by-products and unreacted arylhydroxide or unreacted olefin may include processes such as distillation or crystallization, and combinations thereof, as described by *Chemical and Process Technology Encyclopedia.*, Ed. by D. M. Considine, McGraw-Hill Book Co., 1974, incorporated herein by reference.

During the alkylation, an amount of monosubstituted by-product such as an ether (e.g., cyclohexylphenylether) and an amount of multiple substituted by-product such as a di-adduct (e.g., di-substituted phenol) may be formed. An intermediate product having reduced amounts of di-adducts may be desirably formed by alkylating at a low temperature of about 100° to about 150° C. However, said intermediate product typically has a greater amount of unreacted olefin and monosubstituted by-product. Thus, it is further desirable to remove the unreacted olefin by a technique such as distillation. The monosubstituted ether by-product is also desirably rearranged into the mono-ortho-alkylated arylhydroxide by catalytically rearranging said by-product in the presence of the alkylating catalyst at a temperature greater than the temperature during alkylating, but preferably less than about 300° C. The olefin is preferably removed before the catalytic rearrangement to reduce diadduct formation. The rearrangement is also preferably performed at a temperature of less than about 300° C.

An illustrative example and preferred embodiment of the process described in the previous paragraph is the alkylating of phenol by cyclohexene to form ortho-cyclohexylphenol at a lower temperature to minimize the formation of a disubstituted phenol. A preferable temperature to alkylate is greater than about 100° but less than about 150° C. In addition to the ortho-cyclohexylphenol formed when alkylating at a lower temperature (100°–150° C.), another monosubstituted aryl compound may be formed such as cyclohexylphenyl ether. To minimize formation of disubstituted phenol, any residual cyclohexene is preferably removed before rearranging the cyclohexylphenyl ether. The cyclohexene can be removed by any convenient method such as described hereinabove. The cyclohexylphenyl ether can then be converted to ortho-cyclohexylphenol by rearranging under alkylating conditions described hereinabove with the provision that the temperature is greater than the temperature used to alkylate the phenol. In other words, the temperature to react said cyclohexylphenyl ether is preferably between about 150° to about 300° C.

The second step of the invention is the catalytic dehydrogenation of the intermediate mono-ortho-alkylated arylhydroxide product from the alkylating (first) step of the invention.

The dehydrogenation of the mono-ortho-alkylated arylhydroxide is conducted in the presence of a catalyst which catalyzes the dehydrogenation of an alkylated arylhydroxide to form a mono-ortho-alkenylarylhydroxide or mono-ortho-arylarylhydroxide. Suitable catalysts for the dehydrogenation include catalysts that are described by U.S. Pat. Nos. 5,248,840; 4,080,390; 4,088,702 and 4,060,559 and Japanese Patent Nos. 56-53,632; 49-75,562; 49-41,348 and 49-35,365, each incorporated herein by reference. Preferably the catalyst is a noble metal catalyst. More preferably the catalyst is an oxide supported noble metal catalyst. The oxide support is preferably gamma alumina and more preferably the gamma alumina described hereinabove. The noble metal is preferably platinum. The noble metal is present in a quantity sufficient to catalyze the dehydrogenation reaction. Preferably the quantity of noble metal is about 0.1 to about 5 weight percent of the finished catalyst. To extend catalyst life, it is further preferred to have an alkali or alkaline earth oxide adsorbed onto the oxide support along with the noble metal. Preferably the alkali or alkaline earth oxide is potassium oxide. The quantity of alkali or alkaline earth oxide can be any amount which improves catalyst life compared to a catalyst without said alkali or alkaline earth metal oxide. Preferably the quantity of alkali or alkaline earth metal oxide is about 1 to 15 weight percent of the finished catalyst wherein the finished catalyst comprises the noble metal, oxide support and alkali or alkaline earth metal oxide. More preferably the quantity of alkali or alkaline earth metal oxide is about 2 to 8 weight percent of the finished catalyst.

The oxide supported catalyst can be formed by any convenient method such as those described by U.S. Pat. Nos. 5,248,840; 4,080,390; 4,088,702 and 4,060,559, each incorporated herein by reference. In accordance with this invention, for example, the most preferred catalyst is a gamma alumina supported platinum-potassium oxide catalyst which can be made by precipitation of a compound of platinum and potassium, such as platinum chloride and potassium hydroxide or platinum chloride and potassium carbonate, from an aqueous solution. The platinum and potassium can be precipitated onto the gamma alumina support simultaneously or separately. Typically, the platinum compound is deposited first, heat treated in hydrogen to a temperature of about 300° to about 400° C. for a time to reduce the platinum compound to platinum metal. Then the oxide is deposited and heat treated to a temperature of about 300° C. to about 400° C. to form the oxide.

The reactor used in the dehydrogenation can be a batch or continuous reactor. Preferably the reactor is a continuous reactor such as a tube reactor, and more preferably the continuous reactor for conducting the dehydrogenation is in series with a continuous reactor for conducting the alkylation of this invention. The oxide supported noble metal catalyst can be present in any form in the reactor such as a powder, spheres, cylinders or other geometries. The reaction can be performed with the catalyst as a particulate suspended in the reactants, but it is preferred to have the reactants flow through a catalyst packed bed, particularly in a continuous reactor.

The dehydrogenation step of this invention is run at conditions sufficient to react the mono-ortho-alkylated arylhydroxide to form either a mono-ortho-alkenylarylhydroxide or mono-ortho-arylarylhydroxide. The reaction may be performed at a temperature and pressure wherein the mono-ortho-alkylated arylhydroxide feed is in either a liquid or gas phase. Preferably the dehydrogenation reaction is performed in the gas phase. Preferably the temperature is about 250° C. to about 420° C., more preferably about 300° C. to about 400° C. The pressure of the reaction can be any convenient pressure. The pressure of the dehydrogenation reaction, for practical reasons, is preferred to be atmospheric pressure. The time of the dehydrogenation reaction can be any time sufficient to react the mono-ortho-alkylated arylhydroxide to form a desired mono-ortho-alkenylarylhydroxide or mono-ortho-arylarylhydroxide wherein it is understood the reaction conditions can produce, for example, different levels of unsaturation of the alkenyl of the the mono-ortho-alkenylarylhydroxide. Preferably the time of the reaction (i.e., time at temperature, pressure and contact with catalyst) is about 0.1 to about 4 hours, more preferably about 0.5 to about 3 hours, and most preferably about 1 to about 2 hours. The catalyst lifetime can be extended by known methods such as feeding the reactor with a small amount of hydrogen during the dehydrogenation or regenerating the catalyst by, for example, oxidizing the catalyst in air and thereafter reducing the catalyst with hydrogen at a temperature of about 300° C. to 400° C.

A preferred embodiment of this invention is the reaction of cyclohexene and phenol and subsequent dehydrogenation to form ortho-phenylphenol. The preferred embodiment is carried out by alkylating said cyclohexene and phenol forming ortho-cyclohexylphenol as an intermediate, which is then dehydrogenated to form ortho-phenylphenol wherein at least 50 percent of the phenol is converted into product after alkylating, at least 75 percent of the product formed after alkylating is ortho-cyclohexylphenol, at least 85 percent of the ortho-cyclohexylphenol is converted to product after dehydrogenating and at least 50 percent of the product is ortho-phenylphenol after dehydrogenating. A most preferred embodiment is the above cyclohexene and phenol reaction wherein at least 90 percent of the phenol is converted into product after alkylating, at least 90 percent of the product formed after alkylating is ortho-cyclohexylphenol, at least 95 percent of the ortho-cyclohexylphenol is converted to product after dehydrogenating and at least 85 percent of the product is ortho-phenylphenol after dehydrogenating.

Impurities, by-products and unreacted reactants may be removed from the mono-ortho-alkenylarylhydroxide or mono-ortho-arylarylhydroxide by known techniques such as distillation, crystallization and combinations thereof described hereinbefore.

The ortho-phenylphenol (OPP) produced by the process according to this invention is useful as a germicide, disinfectant, citrus fruit preservative and dye intermediate.

Below are specific examples within the scope of the invention. The specific examples are for illustrative purposes only and in no way limit the invention described herein.

EXAMPLES

Example 1: Formation of Ortho-phenylphenol

Example 1A-Alkylation of phenol with Cyclohexene:

A 1.1 molar phenol/1 molar cyclohexene reactant feed is dried over a MS-5A molecular sieve drying agent until the feed contains less than about 50 ppm water. The feed is reacted at about 180° C. in a stainless steel tube reactor containing Englehard Al-3592 alumina catalyst under a pressure of about 300 psig (20.4 atm.). The catalyst prior to use is activated by heating in air at about 600° C. for about 18 hours. The feed weight/weight catalyst-hour (WHSV) is about 2.

The chemistry of the product in weight percent of the above alkylation reaction is determined by an internal standard gas chromatography method using a DB-5 capillary column. By weight, the product contains about 0.5 percent cyclohexene, 10.3 percent phenol, 0.7 cyclohexyl phenyl ether, 82.4 percent ortho cyclohexyl phenol and 4.7 percent di-adducts wherein di-adducts are molecules identified with having a phenol ring and two cyclohexyl rings.

Example 1B-Dehydrogenation of the product of 1B:

The product of Example 1A is dehydrogenated by passing the product over a dehydrogenating catalyst having a composition of about 0.5 percent by weight Pt, 5 percent by weight KOH on the alumina supported catalyst (Pt-KOH-Alumina catalyst) described above.

The dehydrogenation catalyst is prepared from the same catalyst as described in Example 1A (i.e., Englehard Al-3592 alumina catalyst) by the following method. First, a solution containing about 0.27 gram of dihydrogen hexachloroplatinate is dissolved in 26 mL of deionized water. The solution is added to about 20 grams of alumina catalyst which has been crushed and sieved through a 12–20 mesh screen. The solution-catalyst mixture is dried for about 18 hours. The dried catalyst is heated in hydrogen at about 5° C./min to 300° C. and maintained at 300° C. for 2 hours. The catalyst is then cooled to room temperature and purged with nitrogen. The catalyst is then mixed with a solution containing about 1.0 gram of potassium hydroxide in 26 mL of deionized water. This mixture is again dried for about 18 hours at room temperature in air followed by drying at 100° C. for about 1 hour in air.

The product of Example 1A is reacted in a stainless steel tube reactor containing the Pt-KOH alumina catalyst by first purging the reactor with about 1000 GHSV (volume of gas/volume of catalyst-hr.) of hydrogen at about 350° C. for about 3 hours. Example 1A product preheated to a temperature of about 125° C. is then reacted at a temperature of about 350° C. at a rate of about 1 LHSV (volume of Example 1A product/volume of catalyst-hr.) under atmospheric pressure in a flowing hydrogen gas stream of 100 GHSV. The percent conversion of the orthocyclohexylphenol to ortho-phenylphenol is about 95 percent and the selectivity is about 90 percent.

Example 2: Formation of Ortho-phenylphenol

The alkylation of Example 1A is repeated except the reaction is run at 140° C. The product contains 3.2 percent cyclohexene, 23.3 percent phenol, 13.7 cyclohexylphenyl ether, 57.7 percent ortho cyclohexyl phenol, and about 0.7 percent di-adduct. This product is then distilled in a POPE™

2-inch wiped film still at 170° C., 1.7 psig (0.11 atm.) and 500 rpm (revolutions per minute). The heavies stream (distillation product which is not volatilized off) has about 0.7 percent cyclohexene, 44.3 percent phenol, 15.5 percent cyclohexylphenyl ether, 38 percent ortho cyclohexylphenol and 0.2 percent di-adduct. The heavies stream is reacted under the same conditions as Example 1A, except the reaction temperature is about 235° C. resulting in a product having about 0.05 percent cyclohexene, about 42.7 percent phenol, about 0.05 percent cyclohexylphenyl ether, about 53 percent orthocyclohexyphenol and about 0.4 percent di-adduct. This product from the heavies stream is then reacted under the same conditions as described by Example 1B. Example 1B resulted in essentially the same conversion and selectivity as described in Example 1B.

Examples 3–10

Examples 3–10 are the same as described by Example 1 except that various temperatures for the first step reaction (alkylating) are used as shown in Table 1. Table 1 shows the effect temperature has on the product produced by the alkylating step. The dehydrogenating reaction is performed by the same method described in Example 1B. For each of the Examples in Table 1, the dehydrogenating reaction conversion and selectivity of the OCHP ortho-cyclohexylphenol is essentially the same as the result described in Example 1.

TABLE I

| Example | Alkylating Reaction Temperatures °C. | Wt. % Cyclohexene | Wt. % Phenol | Wt. % CHPE | Wt. % OCHP | Wt. % Di-Adducts |
|---|---|---|---|---|---|---|
| 3 | 120 | 10.4 | 37.3 | 14.7 | 36.6 | — |
| 4 | 130 | 4.9 | 30.9 | 19.1 | 43.2 | 0.4 |
| 5 | 140 | 3.2 | 23.3 | 13.7 | 57.7 | 1.2 |
| 6 | 150 | 1.7 | 17.5 | 7.2 | 70.1 | 2.5 |
| 7 | 160 | 1.2 | 14.3 | 3.9 | 75.8 | 3.7 |
| 8 | 170 | 1.0 | 12.1 | 2.1 | 79.4 | 4.3 |
| 1* | 180 | 0.5 | 10.3 | 0.7 | 82.4 | 4.7 |
| 9 | 190 | 0.5 | 15.9 | 1.0 | 70.7 | 9.8 |
| 10 | 200 | 0.2 | 14.8 | 0.4 | 70.9 | 10.9 |

CHPE = Cyclohexylphenyl ether
OCHP = Ortho-cyclohexylphenol
*Results of alkylating step (Example 1A) of Example 1

The results in Table 1 show that at 180° C. the alkylating reaction has the best conversion to OCHP. Table 1 also shows that the amount of di-adducts can be reduced by reacting at a temperature less than about 150° C. In other words, it is preferable to create OPP via the method described by Example 2 when a low di-adduct concentration in the final OPP product is desired.

Examples 11–13

Examples 11–13 are the same as described by Example 1, except that a temperature of about 215° C. is used for the first reaction step (alkylating) and the reactant feed has various water concentrations as shown in Table 2. Examples 11–13 can be dehydrogenated as described in Example 1.

TABLE II

| Example | Feed Water Concentration (ppm) | % Selectivity | % Conversion |
|---|---|---|---|
| 11 | 50 | 92 | 98 |
| 12 | 150 | 85 | 93 |
| 13 | 300 | <70 | <77 |

The results in Table 2 show that the water concentration in the reactant feed above about 250 ppm (parts per million by weight) results in lower selectivity and lower conversion of the cyclohexene or phenol to OCHP ortho-cyclohexylphenol compared to water contents less than 250 ppm.

What is claimed is:

1. A process to prepare a mono-ortho-arylarylhydroxide or mono-ortho-alkenylarylhydroxide, the process comprising
   (i) alkylating an arylhydroxide having an unsubstituted ortho position with a 2 to 18 carbon olefin in the presence of an alkylating catalyst at a temperature from about 100° C. to about 300° C., a mole ratio of the arylhydroxide to olefin ranging from about 0.5:1 to about 5:1 and a pressure sufficient to form an intermediate product of a mono-ortho-alkylated arylhydroxide and
   (ii) dehydrogenating said mono-ortho-alkylated arylhydroxide in the presence of a dehydrogenating catalyst at a temperature and under conditions sufficient to form a mono-ortho-alkenylarylhydroxide or a mono-ortho-arylarylhydroxide.

2. The process of claim 1 wherein an amount of a mono-substituted ether by-product in the intermediate product is converted to the mono-ortho-alkylated arylhydroxide by removing unreacted olefin from the intermediate product and subsequently catalytically rearranging the ether in the presence of the alkylating catalyst at a rearranging temperature greater than the alkylation temperature.

3. The process of claim 2 wherein the alkylation temperature is between about 100° to 150° C. and the rearranging temperature is less than about 300° C.

4. The process of claim 1 wherein the arylhydroxide is a phenylhydroxide.

5. The process of claim 4 wherein the phenylhydroxide is phenol.

6. The process of claim 1 wherein the olefin is cyclohexene.

7. The process of claim 1 wherein the arylhydroxide is phenol, the olefin is cyclohexene, the ortho-alkylated arylhydroxide is ortho-cylcohexylphenol and the mono-ortho-arylarylhydroxide or mono-ortho-akenylarylhydroxide formed is ortho-phenylphenol.

8. The process of claim 7 wherein at least 50 percent of the phenol is converted into product after alkylating, at least 75 percent of the product formed after alkylating is ortho-cyclohexylphenol, at least 85 percent of the ortho-cyclohexylphenol is converted to product after dehydrogenating and at least 50 percent of the product is ortho-phenylphenol after dehydrogenating.

9. The process of claim 8 wherein at least 90 percent of the phenol is converted into product after alkylating, at least 90 percent of the product formed after alkylating is ortho-cyclohexylphenol, at least 95 percent of the ortho-cyclohexylphenol is converted to product after dehydrogenating and at least 85 percent of the product is ortho-phenylphenol after dehydrogenating.

10. The process of claim 1 wherein the mole ratio is about 1:1 to about 1.1:1.

11. The process of claim 1 wherein step (i) is conducted in the presence of no more than about 150 ppm of water in the arylhydroxide and olefin combined.

12. The process of claim 11 wherein step (i) is conducted in the presence of no more than about 50 ppm of water in the arylhydroxide and olefin combined.

13. The process of claim 1 wherein the alkylating catalyst is an alumina catalyst.

14. The process of claim 13 wherein the alumina catalyst is a gamma alumina catalyst.

15. The process of claim 14 wherein the gamma alumina catalyst is activated by heating to about 400° C. to about 850° C. for about 5 minutes to 100 hours prior to conducting step (i).

16. The process of claim 15 wherein the gamma alumina catalyst has a surface area from about 100 $m^2/g$ to about 300 $m^2/g$.

17. The process of claim 16 wherein the gamma alumina catalyst has at most about 500 ppm metallic impurities.

18. The process of claim 1 wherein the dehydrogenating catalyst is a noble metal catalyst.

19. The process of claim 18 wherein the noble metal catlyst is a gamma alumina supported platinum-potassium oxide catalyst.

20. The process of claim 1 wherein dehydrogenating of the mono-ortho-alkylated arylhydroxide is performed at a temperature of about 250° C. to about 420° C.

21. The process of claim 20 wherein dehydrogenating of the mono-ortho-alkylated arylhydroxide is performed at a temperature of about 300° C. to about 400° C.

22. The process of claim 1 further comprising removing impurites, by-products and unreacted reactants from the mono-ortho-alkenylarylhydroxide or mono-ortho-arylarylhydroxide by distilling or crystallizing said mono-ortho-alkenylarylhydroxide or mono-ortho-arylarylhydroxide.

* * * * *